United States Patent
Tooker et al.

(10) Patent No.: US 9,788,740 B2
(45) Date of Patent: *Oct. 17, 2017

(54) FLEXIBLE NEURAL INTERFACES WITH INTEGRATED STIFFENING SHANK

(71) Applicant: LAWRENCE LIVERMORE NATIONAL SECURITY, LLC, Livermore, CA (US)

(72) Inventors: Angela C. Tooker, Dublin, CA (US); Sarah H. Felix, Oakland, CA (US); Satinderpall S. Pannu, Pleasanton, CA (US); Kedar G. Shah, San Francisco, CA (US); Heeral Sheth, Oakland, CA (US); Vanessa Tolosa, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/208,879

(22) Filed: Jul. 13, 2016

(65) Prior Publication Data

US 2016/0338607 A1 Nov. 24, 2016

Related U.S. Application Data

(62) Division of application No. 14/210,194, filed on Mar. 13, 2014, now Pat. No. 9,399,128.

(Continued)

(51) Int. Cl.
*A61B 5/04* (2006.01)
*A61B 5/00* (2006.01)
(Continued)

(52) U.S. Cl.
CPC ........ *A61B 5/04001* (2013.01); *A61B 5/4076* (2013.01); *A61B 5/6867* (2013.01);
(Continued)

(58) Field of Classification Search
CPC .. A61N 1/0551; A61N 1/0529; A61N 1/3605; A61B 5/04001; A61B 2562/0209; A61B 2562/028; A61B 5/686; A61B 5/6868; A61B 5/6877; A61B 2562/12; A61B 5/6867; A61B 5/4076; A61B 2503/40; A61B 2562/125
See application file for complete search history.

(56) References Cited

U.S. PATENT DOCUMENTS

| 9,399,128 B2 * | 7/2016 | Tooker ................ A61N 1/0551 |
| 2005/0021117 A1 | 1/2005 | He et al. |

(Continued)

FOREIGN PATENT DOCUMENTS

JP 2009285153 12/2009

*Primary Examiner* — Mark W Bockelman
(74) *Attorney, Agent, or Firm* — Eddie E. Scott

(57) ABSTRACT

A neural interface includes a first dielectric material having at least one first opening for a first electrical conducting material, a first electrical conducting material in the first opening, and at least one first interconnection trace electrical conducting material connected to the first electrical conducting material. A stiffening shank material is located adjacent the first dielectric material, the first electrical conducting material, and the first interconnection trace electrical conducting material.

3 Claims, 12 Drawing Sheets

Related U.S. Application Data

(60) Provisional application No. 61/802,382, filed on Mar. 16, 2013.

(51) Int. Cl.
*A61N 1/05* (2006.01)
*A61N 1/36* (2006.01)

(52) U.S. Cl.
CPC ......... *A61N 1/0529* (2013.01); *A61N 1/0551* (2013.01); *A61N 1/3605* (2013.01); *A61B 5/686* (2013.01); *A61B 5/6868* (2013.01); *A61B 5/6877* (2013.01); *A61B 2503/40* (2013.01); *A61B 2562/028* (2013.01); *A61B 2562/0209* (2013.01); *A61B 2562/12* (2013.01); *A61B 2562/125* (2013.01)

(56) References Cited

U.S. PATENT DOCUMENTS

| | | |
|---|---|---|
| 2009/0143848 A1 | 6/2009 | Greenberg et al. |
| 2010/0168830 A1 | 7/2010 | Hung et al. |
| 2011/0054579 A1 | 3/2011 | Kumar et al. |
| 2016/0338607 A1* | 11/2016 | Tooker ................. A61N 1/0551 |

* cited by examiner

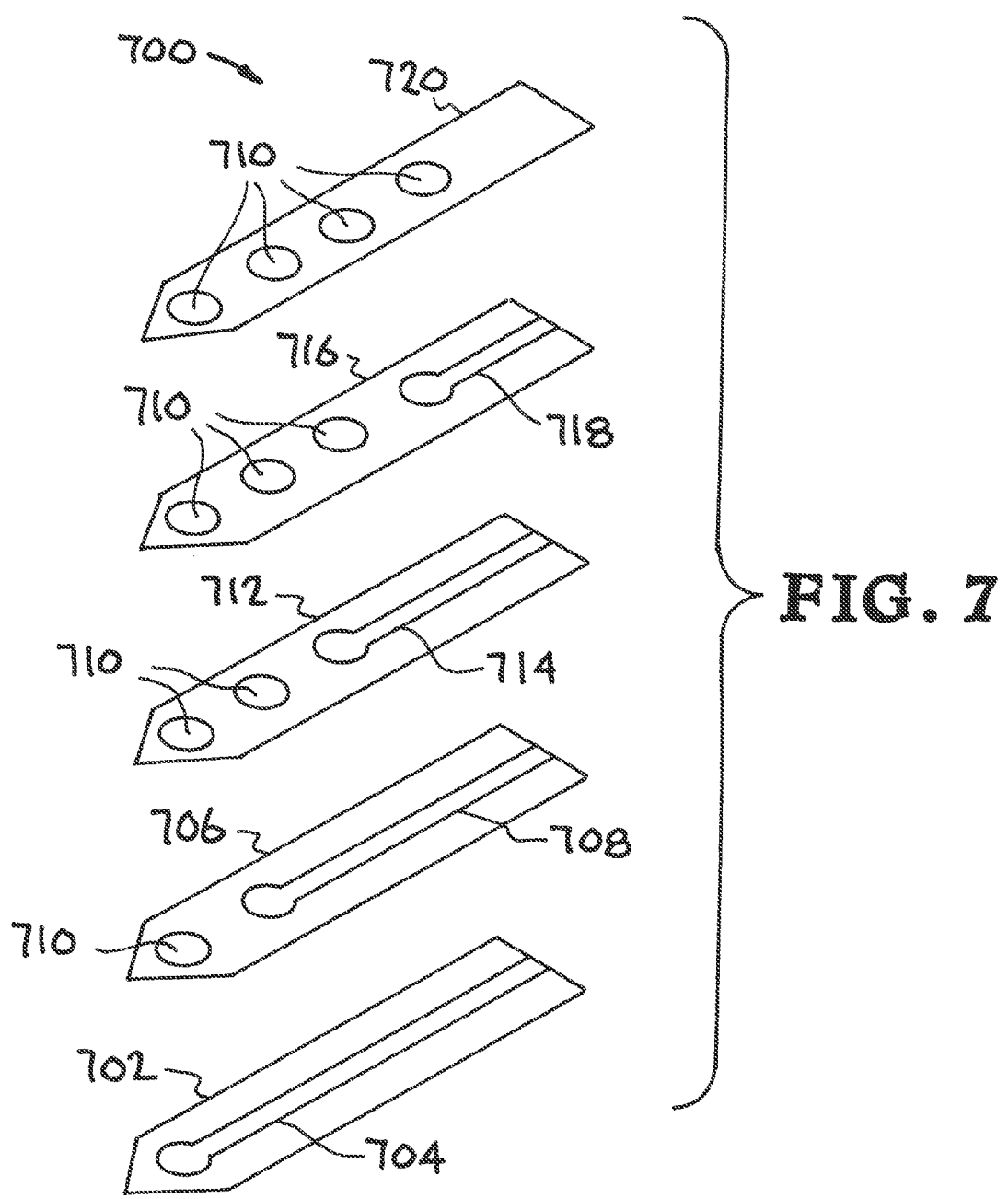

FLEXIBLE NEURAL INTERFACES WITH INTEGRATED STIFFENING SHANK

CROSS-REFERENCE TO RELATED APPLICATIONS

The present application is a Division of application Ser. No. 14/210,194 filed Mar. 13, 2014 entitled "Flexible Neural Interfaces with Integrated Stiffening Shank," which claims benefit under 35 U.S.C. §119(e) of U.S. Provisional Patent Application No. 61/802,382 filed Mar. 16, 2013 entitled "Flexible Neural Interfaces with Integrated Stiffening Shank," the disclosure of which is hereby incorporated by reference in its entirety for all purposes.

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present application relates to microelectrode arrays and methods of fabricating microelectrode arrays, and particularly to a microelectrode array and method of fabricating a microelectrode array such as a neural interface with an integrated stiffening shank.

State of Technology

This section provides background information related to the present disclosure which is not necessarily prior art.

Micro-electrode neural interfaces are an essential tool in neuroscience, targeting the neuronal activity of neurons, enabling researchers and clinicians to better explore and understand neurological diseases. These interfaces use implanted neural probes to bypass damaged tissue and stimulate neural activity, thereby regaining lost communication and/or control with the affected parts of the nervous system.

The most common neural probes are thin-film micromachined probes fabricated on silicon substrates using MEMS fabrication techniques. Neuronal stimulation and recording is conducted at discrete sites (metal pads) along the probes. The metal pads are connected, via metal traces, to output leads or to other signal processing circuitry. Silicon is the most widely used substrate for this type of probe because of its unique physical/electrical characteristics. The prevalence of silicon in the microelectronics industry ensures the neural probes can be relatively easily and efficiently fabricated in large numbers utilizing common MEMS fabrication techniques. There is, however, concern regarding the suitability of these silicon-based neural probes for long-term (i.e. chronic) studies as the silicon will corrode over time when implanted in a body. Furthermore, the continuous micro-motion of the brain can induce strain between the brain tissue and implanted electrode promoting chronic injury and glial scarring at the implant site. Therefore, there are outstanding questions regarding the long-term safety and functionality of these silicon-based neural probes.

Polymer-based neural probes are an attractive alternative. First, they are flexible, thereby minimizing strain between the brain tissue and the implanted probe. Second, they are fully biocompatible and thus suitable for chronic implantation with no loss of functionality or safety. Finally, these polymer-based neural probes can be easily fabricated in large numbers using existing microfabrication techniques.

Unfortunately, the inherent flexibility of the polymer-based neural probes means the probes also have a low mechanical stiffness causing the devices to buckle and fold during insertion. To counteract this, separate stiffening shanks are typically fabricated and then attached to individual neural probes. This procedure is very time-consuming, and in most cases, where the stiffening shanks are extremely thin (<50 µm thick), also very difficult.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

The present application relates to neural interface devices and methods of fabrication of neural interface devices. The neural interface device includes a first dielectric material having at least one first opening for a first electrical conducting material; a first electrical conducting material in the first opening; at least one first interconnection trace electrical conducting material connected to the first electrical conducting material; and a stiffening shank material adjacent the first dielectric material, the first electrical conducting material, and the first interconnection trace electrical conducting material. In one embodiment the method of fabricating a neural interface includes the steps of depositing a bottom dielectric material on a substrate; etching openings in the bottom dielectric material for bottom electrodes; depositing and patterning bottom electrodes; depositing and patterning a bottom interconnection trace metal; depositing an interlayer dielectric material; depositing a stiffening shank material; depositing an interlayer dielectric material; patterning a stiffening shank from the stiffening shank material; depositing an interlayer dielectric material; depositing and patterning a top interconnection trace metal; depositing and patterning top electrodes; depositing a top dielectric material; etching openings in the top dielectric material for the top electrodes and connector openings; and releasing the device from the substrate.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

FIG. 7 illustrates another embodiment of Applicant's apparatus, system and method.

DETAILED DESCRIPTION OF SPECIFIC EMBODIMENTS

Figure 1A:
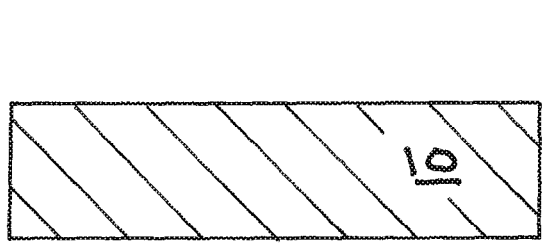
FIGS. 1A through 1O illustrate embodiments of Applicant's apparatus, system and method.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

The apparatus, systems, and methods described and claimed herein enable combining of a polymer-based neural probe with an integrated stiffening shank. With the apparatus, systems, and methods described and claimed herein polymer-based neural probes are created with a stiffened area suitable for insertion into tissue but also with a flexible cable to minimize tissue damage. Utilizing existing microfabrication techniques, large numbers of stiffened polymer-based neural probes can be created easily and efficiently. The flexible neural interface with integrated stiffening shank described and claimed herein is suitable for implantation in both humans and animals for either acute or chronic studies of various neurological disorders and as interfaces between neural tissue and prosthetics. (This assumes the materials comprising the device have been properly chosen with regards to their biocompatibility.) The neural probes described and claimed herein have a flexible, polymer-based cable, which runs the length of the probe and contains the electrodes and interconnection traces and a stiffening shank at the tip (where the electrodes are located). The stiffening shank is built into the device utilizing standard microfabrication techniques, and requires no post-fabrication attachment. There are different versions of the flexible neural interface with integrated stiffening shank for example a fully-encapsulated stiffening shank and a partially-encapsulated stiffening shank. (The partially-encapsulated stiffening shank may not be suitable for chronic studies.) These neural interfaces can be created with electrodes on the "top," on the "bottom," or on both the "top" and "bottom."

In addition to being an integrated, wafer-level process, another advantage of this process is that the stiffening shank is not limited to silicon, unlike traditional non-polymer based neural interfaces. Other materials, with varying mechanical properties, can also be used, such as other semiconductors, dielectrics (e.g. glass/quartz/silicon-dioxide, sapphire), ceramics (e.g. alumina), metals (e.g. titanium, tungsten), and others (e.g. silicon-carbide, diamond). Ultimately, the mechanical properties and the thickness of the material used for the stiffening shank dictate the stiffness of the neural interface. Further, the process is not limited to vapor-deposited (e.g. sputtering, electron-beam/thermal evaporation, atomic layer deposition, chemical vapor deposition, physical vapor deposition) materials and thicknesses. The encapsulation process allows free-standing films (e.g. metal foils) to be used.

This disclosure describes a fully-integrated fabrication process for flexible neural interfaces with integrated stiffening shanks. These neural interfaces are suitable for implantation in both humans and animals for either acute or chronic studies of various neurological disorders (e.g. Clinical Depression, Parkinson's Disease, Epilepsy) and as interfaces between neural tissue and prosthetics (e.g. Retinal Implants, Auditory Implants).

In one embodiment the device disclosed in the present application is a microelectrode array, such as a neural interface, with an integrated stiffening shank having electrodes on the top or having electrodes on the bottom or having electrodes both on the top and on the bottom. In another embodiment, the present application relates to a microelectrode array fabrication method and in particular to a microelectrode neural interface fabrication method and method of fabricating a microelectrode array with an integrated stiffening shank. Other example implementations provide a microelectrode array having an electrical conduit embedded within a simultaneously-polymerized multi-polymer precursor layer-based, single polymer film, wherein a portion of the conduit is exposed through the single polymer film.

The flexible neural interface with integrated stiffening shank described here is suitable for implantation in both humans and animals for either acute or chronic studies of various neurological disorders and as interfaces between neural tissue and prosthetics. The neural probes described here have a flexible, polymer-based cable, which runs the length of the probe and contains the electrodes and interconnection traces and a stiffening shank at the tip (where the electrodes are located). The stiffening shank is integrated into the device utilizing standard microfabrication techniques, and requires no post-fabrication attachment.

Figure 1B:
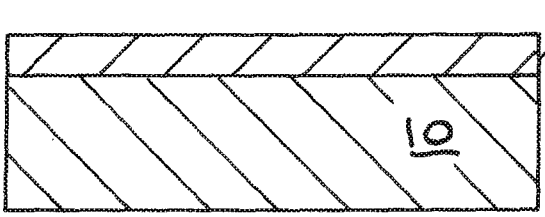
Figure 1C:
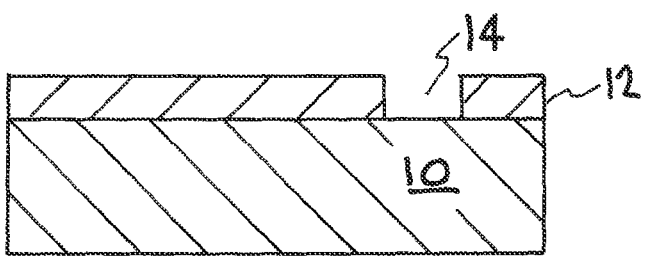
Figure 1D:
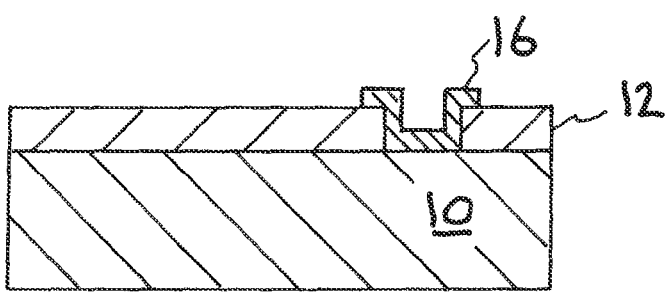
Figure 1E:
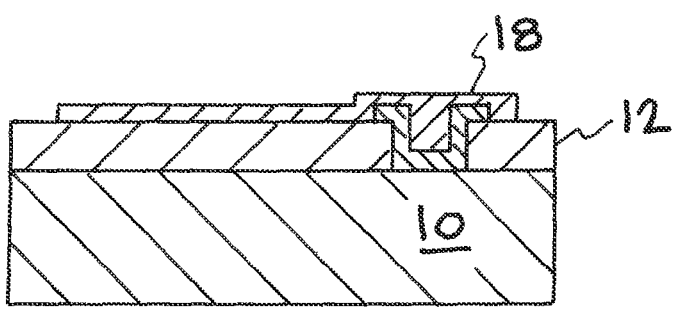
Figure 1F:
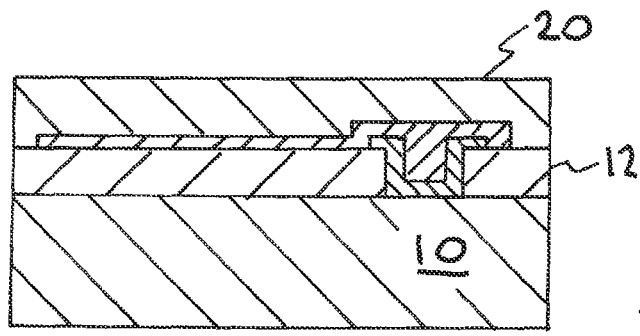
Figure 1G:
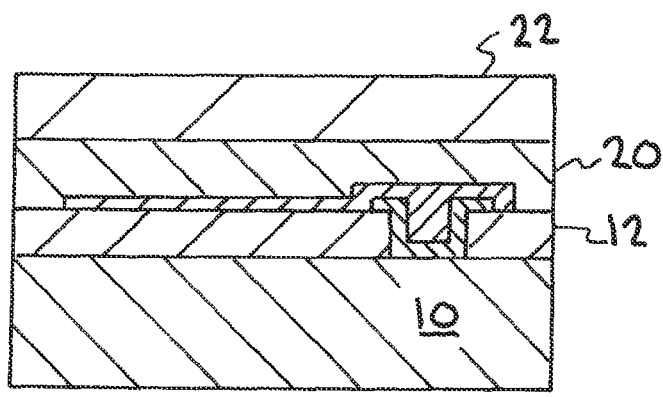
Figure 1H:
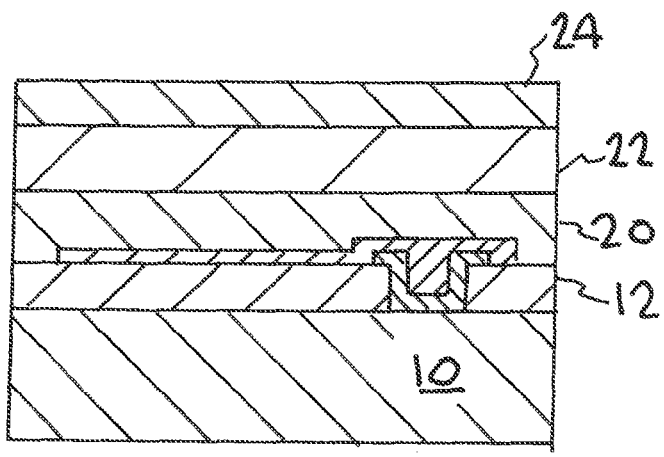
Figure 1I:
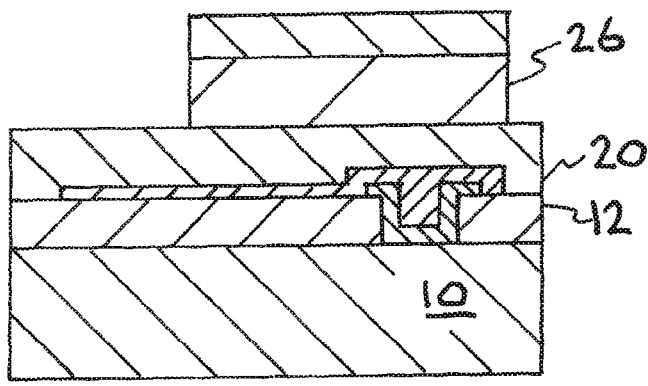
Figure 1J:
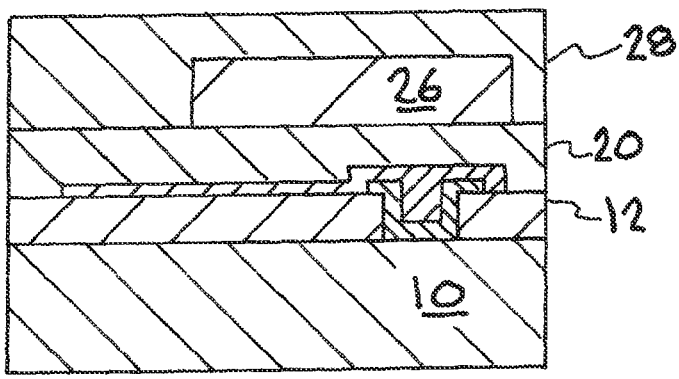
Figure 1K:
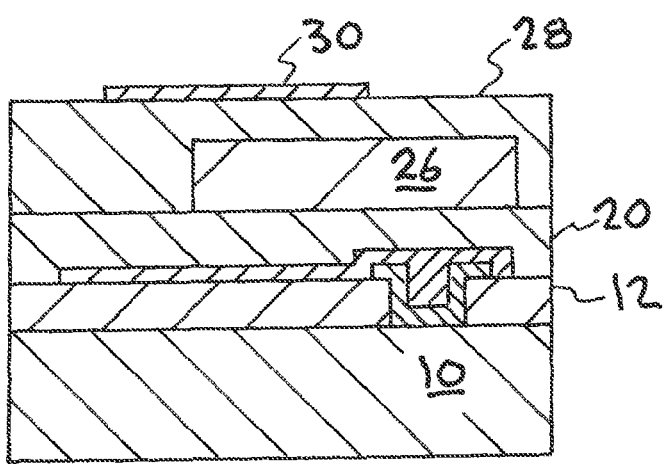
Figure 1L:
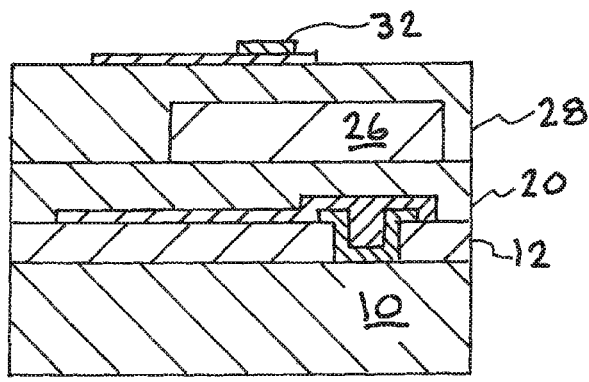
Figure 1M:
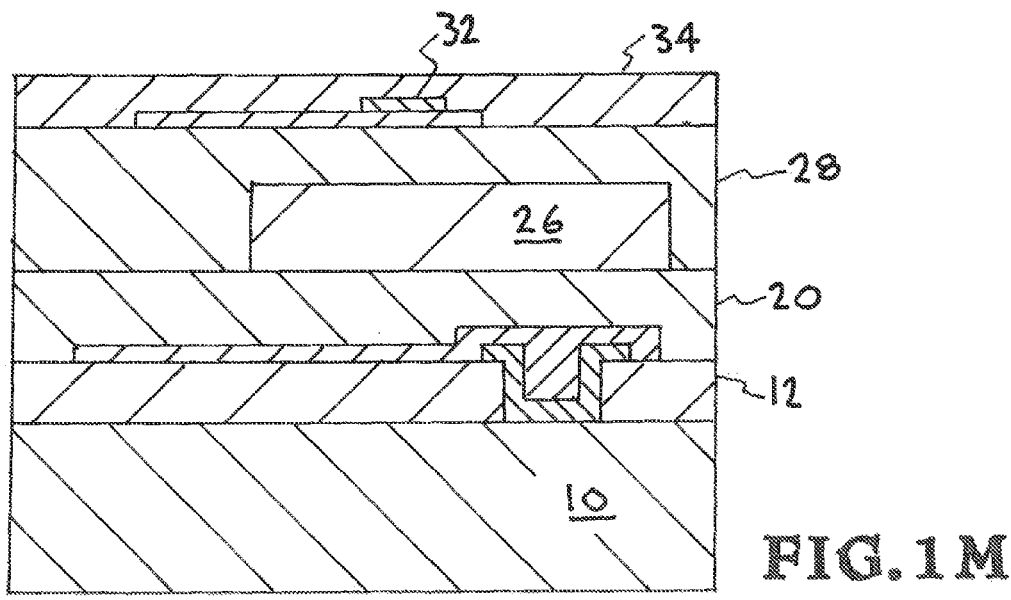
Figure 1N:
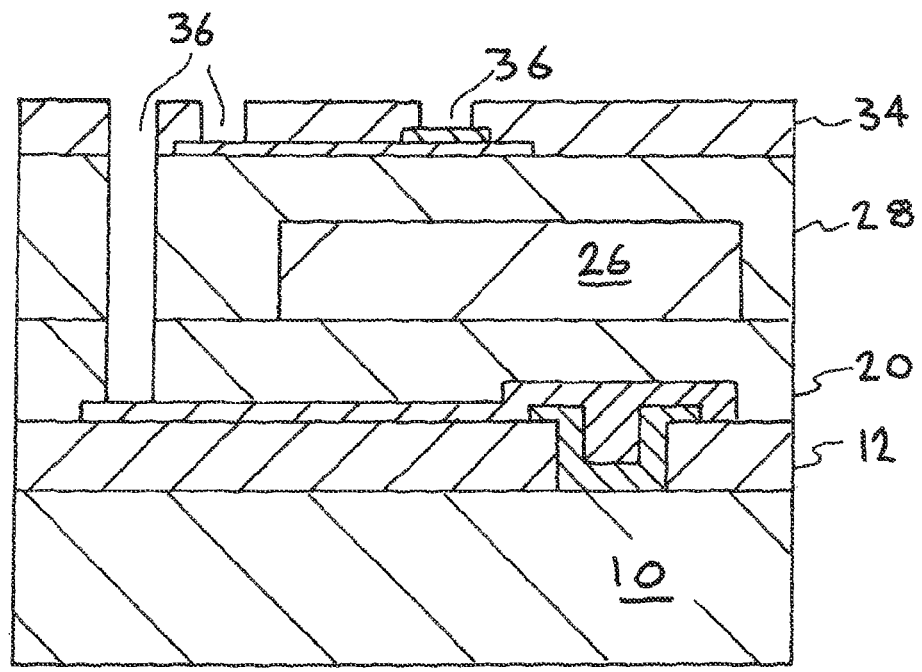
Figure 1O:
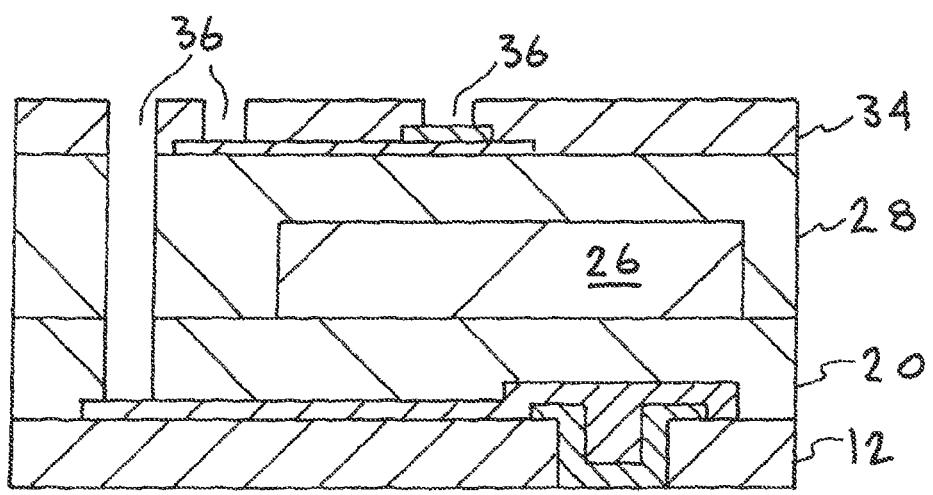

Referring now to the drawings and in particular to FIGS. 1A-1O, one embodiment of Applicant's apparatus, system and method is illustrated. This embodiment of Applicant's apparatus, system and method is designated generally by the reference numeral 100 shown in FIG. 1A.

A substrate 10 is shown in FIG. 1A. Silicon can be used as the substrate material or other material can be used as the substrate material provided the material is compatible with the techniques and chemicals used during the microfabrication. In some cases, a release layer (e.g. chrome) is deposited on the starting substrate 10 prior to the first step of the fabrication process to ensure an easy release of the final device.

A bottom polymer 12 is deposited on the substrate 10. This is shown in FIG. 1B wherein the bottom polymer 12 is shown deposited on the substrate 10.

An opening 14 is etched in the bottom polymer for the bottom electrodes. This is shown in FIG. 1C wherein the opening 14 for the bottom electrodes has been etched in the bottom polymer 12.

The bottom electrodes are deposited and patterned. This is shown in FIG. 1D wherein the deposition and patterning of the bottom electrodes is illustrated. The material 16 for the bottom electrodes is deposited and patterned.

Interconnection trace metal 18 is deposited and patterned. This is shown in FIG. 1E wherein the interconnection trace metal 18 of the bottom electrodes is illustrated.

An interlayer polymer 20 is deposited on the bottom polymer 12. This is shown in FIG. 1F wherein the interlayer polymer 20 is shown deposited on the bottom polymer 12 and the interconnection trace metal 18.

Stiffening shank material 22 is deposited on the interlayer polymer 20. This is shown in FIG. 1G wherein the stiffening shank material 22 is shown deposited on the interlayer polymer 20.

An interlayer polymer 24 is deposited on the stiffening shank 22. This is shown in FIG. 1H wherein the interlayer polymer 24 is shown deposited on the stiffening shank 22.

The stiffening shank material 22 is patterned to produce a patterned stiffening shank 26. This is shown in FIG. 1I wherein the patterned stiffening shank 26 is shown on the interlayer polymer 20.

An interlayer polymer 28 is deposited on the patterned stiffening shank 26. This is shown in FIG. 1J wherein the interlayer polymer 28 is shown deposited on the patterned stiffening shank 26 and the interlayer polymer 20.

Interconnection trace metal 30 is deposited and patterned. This is shown in FIG. 1K wherein the interconnection trace metal 30 of the top electrodes is illustrated.

Patterned top electrode metal 32 is deposited and patterned. This is shown in FIG. 1L wherein the patterned top electrode metal 32 is illustrated.

A top polymer 34 is deposited on the top electrode metal 32. This is shown in FIG. 1M wherein the top polymer 34 is shown deposited on the top electrode metal 32 and interlayer polymer 28.

Openings 36 are etched in the top polymer for the top electrodes and external connections. This is shown in FIG. 1N wherein the openings 36 for the top electrodes and external connections have been etched.

The final release of the device is illustrated in FIG. 1O. The substrate 10 has been removed as shown in FIG. 1O.

Figure 2A:
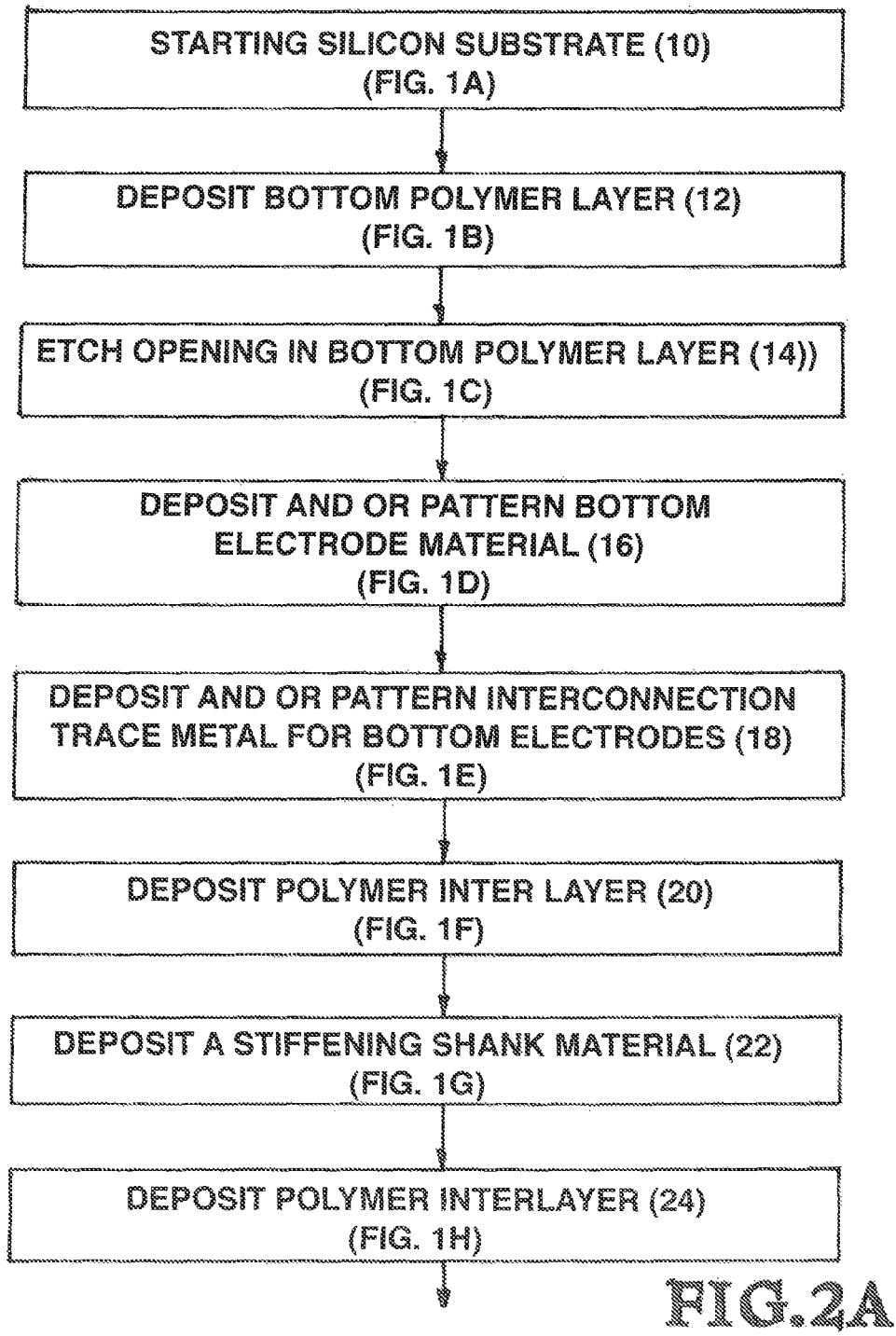
FIGS. 2A and 2B provide a flow chart illustrating one embodiment of a process of fabricating a neural interface.
Figure 2B:
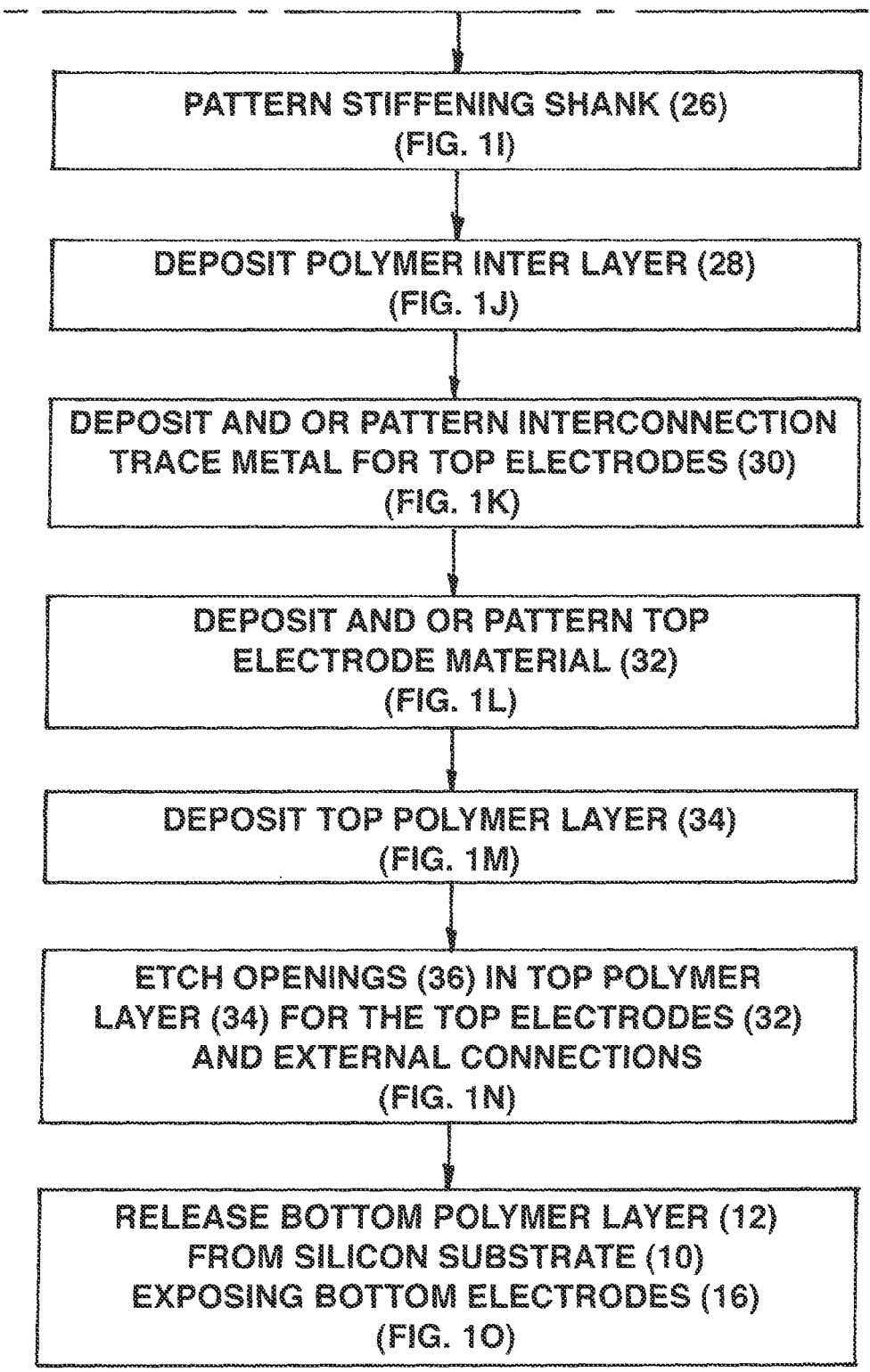

Referring now to FIGS. 2A and 2B, the flow chart illustrates the process of fabricating a neural interface with integrated stiffening shank and electrodes on both the top and bottom surfaces. FIG. 2A shows the steps beginning with the starting silicon substrate 10. Silicon can be used as the substrate material or other material can be used as the substrate material provided the material is compatible with the techniques and chemicals used during the microfabrication. In some cases, a release layer (e.g. chrome) is deposited on the starting substrate 10 prior to the first step of the fabrication process to ensure an easy release of the final device.

In the next step a bottom polymer 12 is deposited on the substrate 10.

In the next step an opening 14 is etched in the bottom polymer for the bottom electrodes.

In the next step the bottom electrodes are deposited and patterned. The material 16 for the bottom electrodes is deposited and patterned.

In the next step interconnection trace metal 18 is deposited and patterned.

In the next step an interlayer polymer 20 is deposited on the bottom polymer 12 and the interconnection trace metal 18.

In the next step a stiffening shank material 22 is deposited on the interlayer polymer 20.

In the next step an interlayer polymer 24 is deposited on the stiffening shank material 22.

Referring now to FIG. 2B, the additional steps for fabricating a neural interface with integrated stiffening shank and electrodes on both the top and bottom surfaces are shown.

In the next step the stiffening shank material 22 is patterned to produce a patterned stiffening shank 26.

In the next step an interlayer polymer 28 is deposited on the patterned stiffening shank 26 and interlayer polymer 20.

In the next step interconnection trace metal 30 is deposited and patterned.

In the next step patterned top electrode metal 32 is deposited and patterned.

In the next step a top polymer 34 is deposited on the top electrode metal 32 and interlayer polymer 28.

In the next step openings 36 are etched in the top polymer for the top electrodes and external connections.

The next step is the final release of the device. The substrate 10 has been removed.

The process described above (FIGS. 1A-1O and FIGS. 2A-2B) creates a neural interface with electrodes on both the top and bottom surfaces. If electrodes are only desired on the top surface, then the appropriate steps can be eliminated. If electrodes are only desired on the bottom surface, then the appropriate steps can be eliminated.

The process is also compatible with different locations of the electrode metal, with respect to the outer polymer layers, by appropriate re-arrangement of steps. As shown in the process described above, the bottom electrodes are flush with the bottom polymer layer and the top electrodes are underneath the top polymer layer (i.e. effectively recessed from the top polymer layer). In another example implementation, the top electrodes can be on top of the top polymer layer by depositing and patterning them after the openings in the top polymer layer. In another example implementation, posts in the substrate material can be etched at the electrode locations prior to the deposition of the bottom polymer layer. This has the effect of recessing the bottom electrodes from the bottom polymer surface. In another example implementation, the bottom electrode material can be deposited before the bottom polymer layer, which has the effect of putting the bottom electrodes on the outside of the device (i.e. the bottom polymer layer). These different top and bottom electrode locations, with respect to the polymer layers, can be mixed and matched with this process to create a variety of different neural interfaces.

The process described above creates a neural interface with only two layers of interconnection trace metal (one for the top electrodes and one for the bottom electrodes). This same process can be used with multiple layers of interconnection trace metal for both the top and bottom electrodes. Each additional interconnection trace metal layer requires the use of another interlayer polymer layer (with appropriate openings between the interconnection trace metal layers). Different numbers of interconnection trace metal layers can be used for the top and bottom electrodes. One example would be a process/interface in which the top electrodes use 3 layers of interconnection trace metal and the bottom electrodes use 4 layers of interconnection trace metal.

The outlined fabrication steps are independent of the neural interface dimensions (length, width, thickness, overall shape) and the electrode properties (number, spatial arrangement, thickness, shape, material).

The fabrication process is independent of the specific type of polymer used to create the neural interface. Polymides and parylenes (poly(p-xylylene) are the two most commonly used polymers due to their biocompatibility. Other polymers can be used (provided these materials can be deposited and etched), although these other polymers may not be biocompatible and, thus, the neural interfaces created with these materials may not be suitable for chronic and/or acute implantation studies.

The fabrication process is independent of the specific materials used for the interconnection trace metals and the electrode metals. Although metals (e.g. gold, titanium, platinum, iridium) are the most common, due to their ease of deposition and patterning, any conductive material (e.g. other metals, conductive polymers, conductive inks) can be used. In addition, although it is shown that separate metal layers are used for the electrode metal and interconnection trace metal, this fabrication process allows a single material to be used for both the electrode metal and interconnection trace metal by elimination of the electrode metal deposition and patterning steps. This fabrication process does not require each metal layer (interconnection trace metal or electrode metal) to be comprised of the same material. A different conductive material can be used for each metal layer to meet the desired electrical and mechanical specifications.

The fabrication process is also independent of the specific material used for the stiffening shank. It is also independent of the dimensions (length, width, thickness, overall shape) of the stiffening shank. Any material that can be deposited and etched can be used. For Version 1 of the device (Fully-Encapsulated), the final device should be biocompatible and suitable for chronic and acute implantation studies, regardless of whether the stiffening shank material is biocompatible (provided the chosen polymer is biocompatible). For Version 2 of the device (Partially-Encapsulated), unless the stiffening shank material is biocompatible, the neural interface created may not be biocompatible and therefore may not be suitable for chronic and/or acute implantation studies.

Figure 3A:
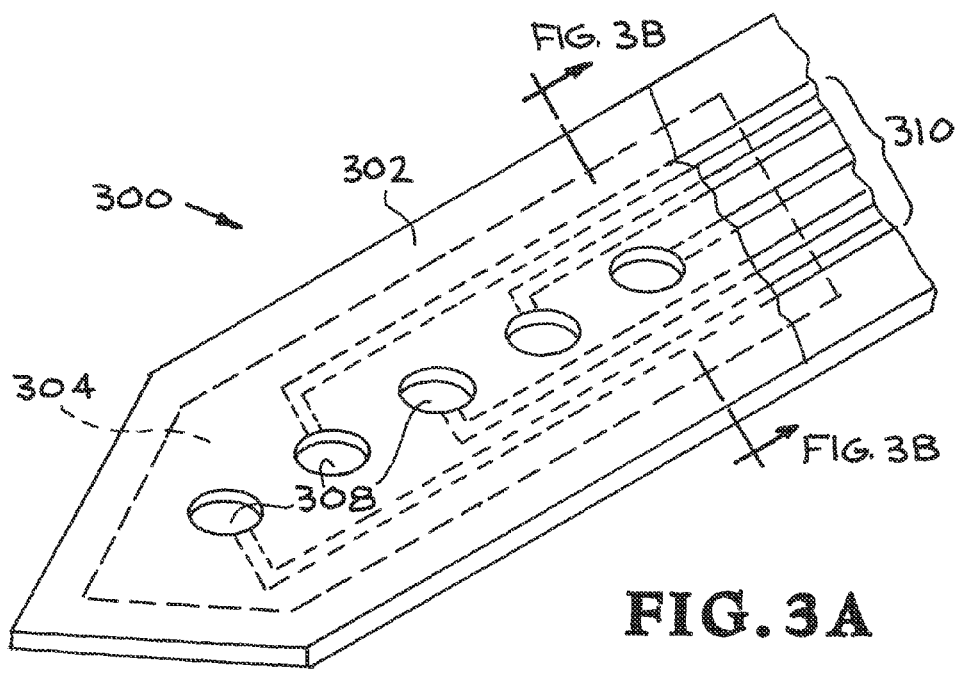
FIGS. 3A and 3B illustrate one embodiment of a fully-encapsulated integrated stiffening shank.
Figure 3B:
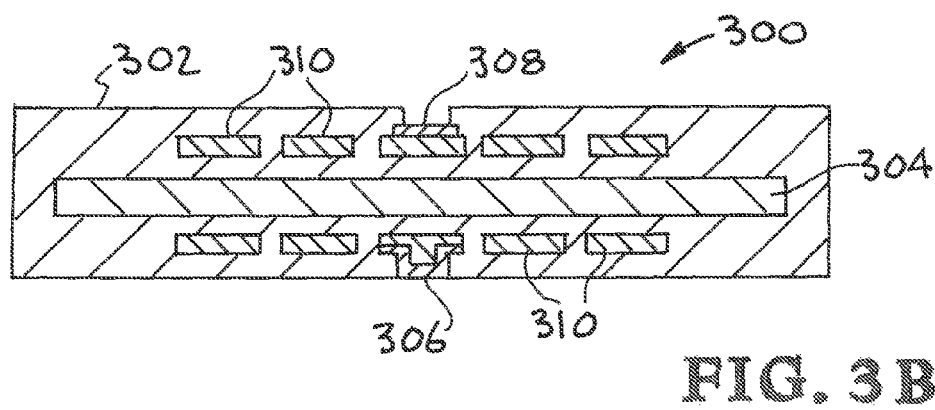

Referring now to FIGS. 3A and 3B a fully-encapsulated integrated stiffening shank is illustrated. The fully-encapsulated integrated stiffening shank is designated generally by the reference numeral 300. The material used for the integrated stiffening shank does not need to be biocompatible, as once the fabrication process is complete, the integrated stiffening shank is not exposed. Provided the chosen polymer for the flexible neural interface is biocompatible, the finished device should be biocompatible and suitable for long-term implantation.

FIGS. 3A and 3B are top-down (top) and cross-section (bottom) views of the flexible neural interface with a fully-encapsulated integrated stiffening shank. The cross-section view 3B shows the cross section of the device 300 through the line and arrows specified in FIG. 3A. The device 300 has a multilayer body 302. The device 300 has an integrated shank 304. The bottom electrodes 306 are flush with the bottom polymer layers and the top electrodes 308 are recessed from the top polymers layers. The electrodes are sandwiched between the polymer layers and connected by traces 310. For simplicity, the connector region of the device is not shown. The integrated stiffening shank is only at the tip of the device (at the electrode regions) where the device will be inserted. The integrated stiffening shank does not extend the full length of the polymer cable.

Figure 4A:
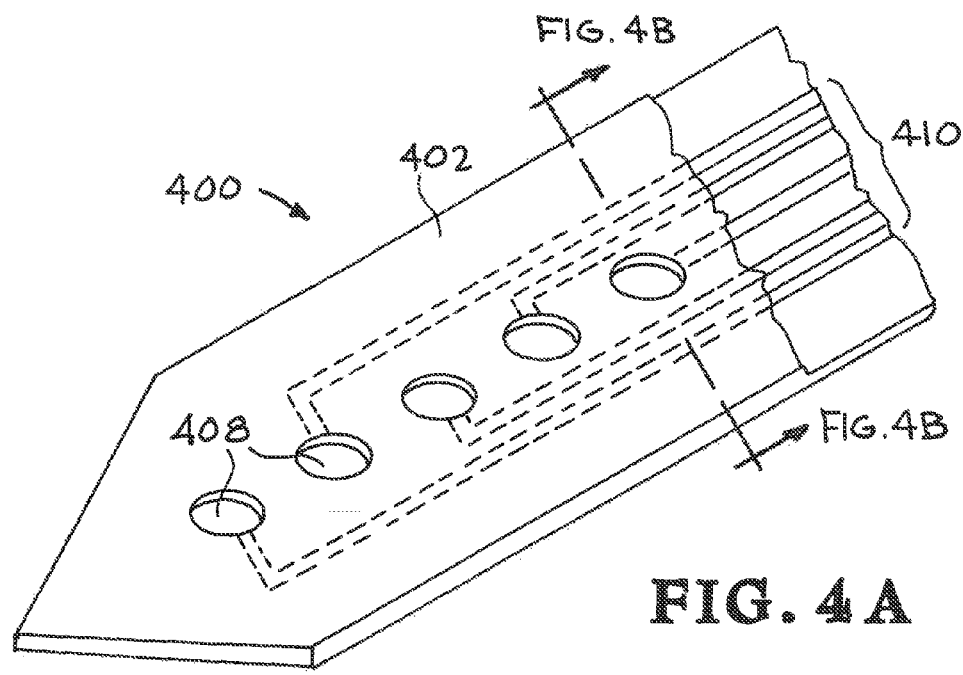
FIGS. 4A and 4B illustrate one embodiment of a partially encapsulated integrated stiffening shank.
Figure 4B:
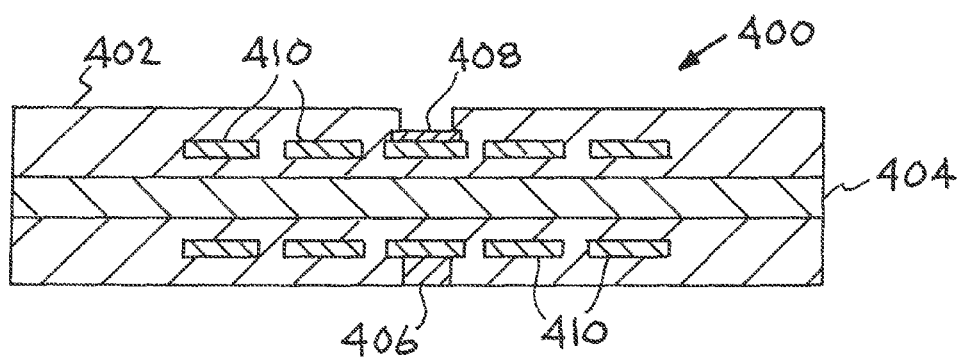

Referring now to FIGS. 4A and 4B a partially encapsulated integrated stiffening shank is illustrated. The partially encapsulated integrated stiffening shank is designated generally by the reference numeral 400. To ensure biocompatibility of the final device, and suitability for chronic and/or acute implantation studies, the stiffening shank material must be biocompatible because in this implementation the stiffening shank is not fully encapsulated.

FIGS. 4A and 4B are top-down (top) and cross-section (bottom) views of the flexible neural interface with a partially-encapsulated integrated stiffening shank. The cross-section view 4B shows the cross section of the device 400 through the line and arrows specified in FIG. 4A. The device 400 has a multilayer body 402. The device 400 has an integrated shank 404. The bottom electrodes 406 are flush with the bottom polymer layers and the top electrodes 408 are recessed from the top polymers layers. The electrodes are sandwiched between the polymer layers and connected by traces 410. For simplicity, the connector region of the device is not shown. The integrated stiffening shank is only at the tip of the device (at the electrode regions) where the device will be inserted. The integrated stiffening shank does not extend the full length of the polymer cable.

Figure 5A:
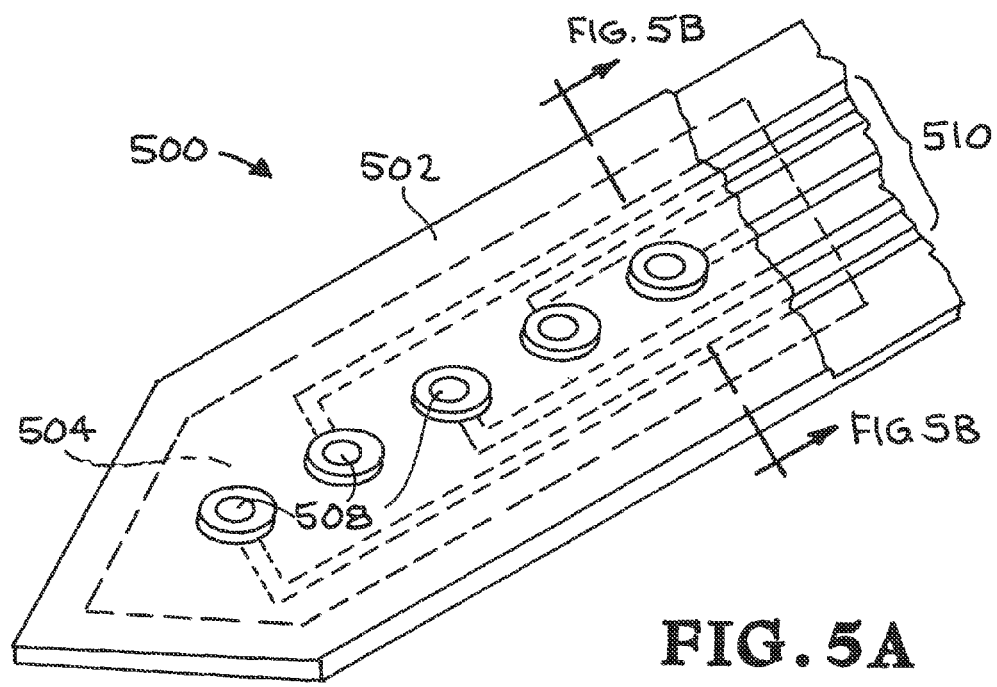
FIGS. 5A and 5B illustrate another embodiment of a fully-encapsulated integrated stiffening shank.
Figure 5B:
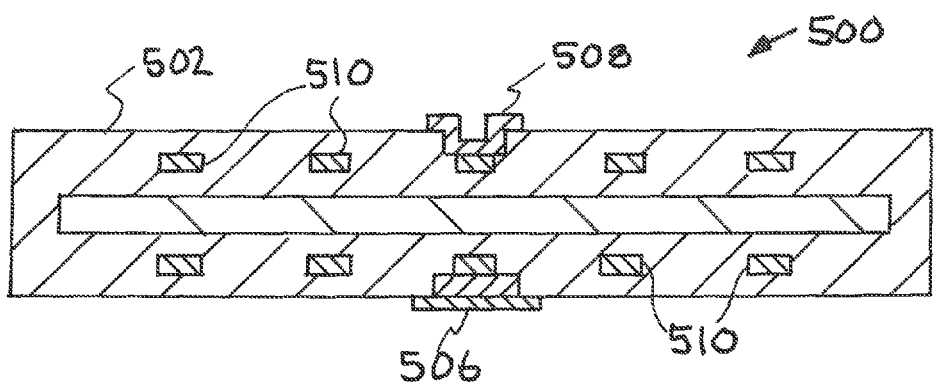

Referring now to FIGS. 5A and 5B a fully-encapsulated integrated stiffening shank is illustrated. The fully-encapsulated integrated stiffening shank is designated generally by the reference numeral 500. The material used for the stiffening shank does not need to be biocompatible, as once the fabrication process is complete, the stiffening shank is not exposed. Provided the chosen polymer for the flexible neural interface is biocompatible, the finished device will also be biocompatible and suitable for long-term implantation.

FIGS. 5A and 5B are top-down (top) and cross-section (bottom) views of the flexible neural interface with a fully-encapsulated integrated stiffening shank designated by the reference numeral 504 that encapsulated by an encapsulating polymer designated by the reference numeral 504. The cross-section view 5B shows the cross section of the device 500 through the line and arrows specified in FIG. 5A. In this device 500, the bottom electrode 506 is outside the polymer layer. The top electrode 508 is outside the polymer layers. Although not shown, the same electrode arrangement can also be made with a partially-encapsulated integrated stiffening shank. The integrated stiffening shank is only at the tip of the device (at the electrode regions) where the device will be inserted. The integrated stiffening shank does not extend the full length of the polymer cable.

Figure 6A:
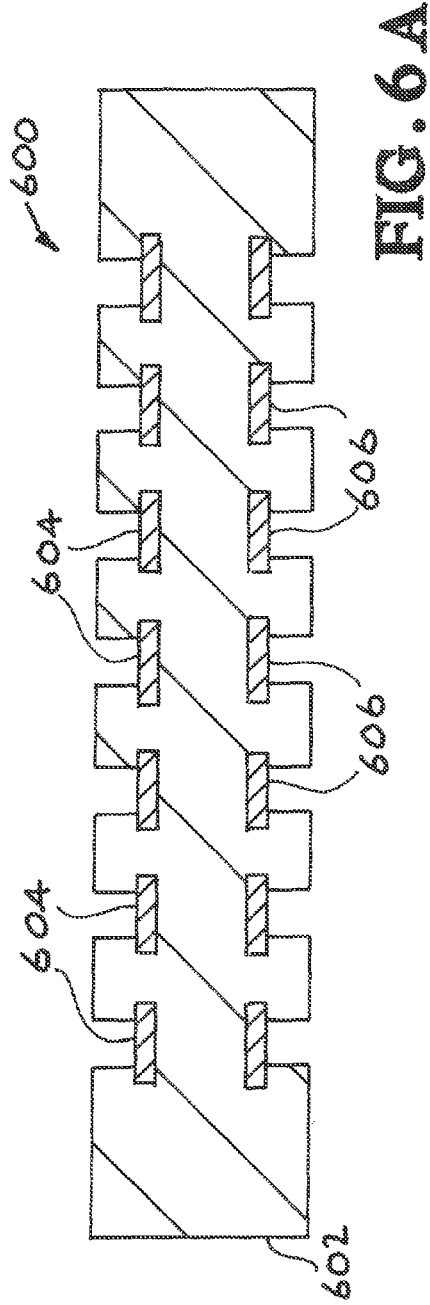
FIGS. 6A and 6B illustrate the fabrication processes independent of the electrode spatial arrangement.
Figure 6B:
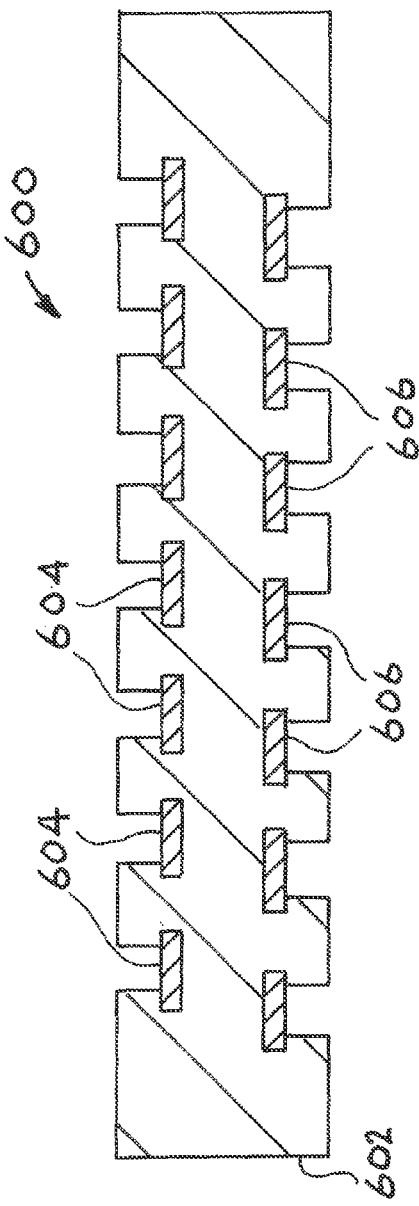

Referring now to FIGS. 6A and 6B the fabrication processes presented here is shown independent of the electrode spatial arrangement. This is designated generally by the reference numeral 600. The top electrodes 604 and the bottom electrodes 606 can be overlaid directly on top of each other (6A) or offset from each other (6B). Both layers of electrodes (top and bottom) can be arranged independently in a variety of ways (i.e. straight lines, grouped together), with different inter-electrode spacings, shapes (i.e. circular, oval, square, rectangular), and sizes. It is possible to create a variety of differently shaped and sized electrodes on a single neural interface.

Referring now to FIG. 7 another embodiment of Applicant's apparatus, system and method are illustrated. The neural interface device is designated generally by the reference numeral 700. The neural interface device 700 is a multi-layered device that includes a bottom layer 702 of dielectric material with an electrical conducting material 704. The intermediate layer 706 consists of a dielectric material with an electrical conducting material 708 and an electrode 710. The intermediate layer 712 consists of a dielectric material with an electrical conducting material 714 and electrodes 710. The intermediate layer 716 consists of a dielectric material with an electrical conducting material 718 and electrodes 710. The top layer 720 consists of a dielectric material with 710.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. A neural interface device adapted to be inserted into tissue, comprising:
   a neural interface body, wherein said neural interface body includes
   an insertion end and
   a body portion extending from said insertion end;
   an upper layer made of a first biocompatible dielectric material having at least one first opening for a first electrical conducting material;
   said upper layer extending over said insertion end and said body portion of said neural interface body wherein said at least one first opening for a first electrical conducting material is located in said upper layer extending over said insertion end;
   a first electrical conducting material in said first opening;
   an electrode positioned over said at least one first opening and over said first electrical conducting material in said first opening;
   at least one first interconnection trace electrical conducting material in said upper layer connected to said first electrical conducting material, wherein said at least one first interconnection trace electrical material is located in said upper layer extending over said insertion end and said body portion of said neural interface body;
   a lower layer made of a second dielectric material wherein said second dielectric material is biocompatible, wherein said lower layer extends under said insertion end and said body portion of said neural interface body; and
   a stiffening shank between said upper layer and said lower layer wherein said stiffening shank is adjacent said first dielectric material, said first electrical conducting material, and said first interconnection trace electrical conducting material, wherein said stiffening shank is made of a material that provides the neural interface device with sufficient stiffening that the neural interface device is adapted to be inserted into tissue, and wherein said stiffening shank is located only in said insertion end of said neural interface body.

2. A neural interface device adapted to be inserted into tissue of claim 1 wherein said first electrical conducting material in said first opening is made of metal.

3. A neural interface device adapted to be inserted into tissue of claim 1 wherein said first electrical conducting material in said first opening is made of a conducting polymer.

* * * * *